(12) United States Patent
Hammerslag

(10) Patent No.: US 6,723,095 B2
(45) Date of Patent: Apr. 20, 2004

(54) METHOD OF SPINAL FIXATION USING ADHESIVE MEDIA

(75) Inventor: Julius G. Hammerslag, San Juan Capistrano, CA (US)

(73) Assignee: Hemodynamics, Inc., La Quinta, CA (US)

( * ) Notice: Subject to any disclaimer, the term of this patent is extended or adjusted under 35 U.S.C. 154(b) by 0 days.

(21) Appl. No.: 10/041,652

(22) Filed: Dec. 28, 2001

(65) Prior Publication Data

US 2003/0125737 A1 Jul. 3, 2003

(51) Int. Cl.[7] .................. A61B 17/56; A61B 17/58; A61F 2/28; A61F 2/30
(52) U.S. Cl. .................. 606/60; 623/23.62
(58) Field of Search .................. 606/53, 60, 61, 606/62, 63, 92, 93, 94; 623/23.57, 23.58, 23.59, 23.6, 23.61, 23.62, 17.11, 17.15, 17.16

(56) References Cited

U.S. PATENT DOCUMENTS

| 5,037,437 A | * | 8/1991 | Matsen, III | 623/16 |
| 5,053,046 A | | 10/1991 | Janese | |
| 5,290,558 A | | 3/1994 | O'Leary et al. | |
| 5,415,661 A | * | 5/1995 | Holmes | 606/69 |
| 5,443,514 A | | 8/1995 | Steffee | |
| 5,498,259 A | | 3/1996 | Mourant et al. | |
| 5,888,220 A | * | 3/1999 | Felt et al. | 623/17 |
| 5,980,504 A | * | 11/1999 | Sharkey et al. | 604/510 |
| 5,980,522 A | * | 11/1999 | Koros et al. | 606/61 |
| 6,007,570 A | * | 12/1999 | Sharkey et al. | 607/96 |
| 6,031,069 A | | 2/2000 | Oberhoffner et al. | |
| 6,037,519 A | | 3/2000 | McKay | |
| 6,130,271 A | | 10/2000 | Jarrett et al. | |
| 6,183,516 B1 | | 2/2001 | Burkinshaw et al. | |
| 6,211,335 B1 | | 4/2001 | Owen et al. | |
| 6,224,622 B1 | | 5/2001 | Kotzev | |
| 6,309,420 B1 | * | 10/2001 | Preissman | 623/16.11 |
| 6,369,164 B1 | * | 4/2002 | Klee et al. | 525/285 |
| 6,375,659 B1 | * | 4/2002 | Erbe et al. | 606/94 |
| 6,386,203 B1 | * | 5/2002 | Hammerslag | 128/898 |
| 6,428,576 B1 | * | 8/2002 | Haldimann | 623/17.16 |
| 2002/0016583 A1 | * | 2/2002 | Cragg | 604/500 |

FOREIGN PATENT DOCUMENTS

| GB | 2169906 A | * | 7/1986 | C08K/3/24 |
| WO | WO 99/30629 | | 12/1998 | |

* cited by examiner

Primary Examiner—Eduardo C. Robert
Assistant Examiner—Anuradha Ramana
(74) Attorney, Agent, or Firm—Knobbe, Martens, Olson & Bear, LLP.

(57) ABSTRACT

Disclosed are methods of spinal fixation involving application of a liquid medium which cures, hardens, polymerizes or otherwise serves to bind adjacent vertebrae together. The fixation which results from this binding may be temporary or essentially permanent in duration, and may be used to treat conditions or disease of the spine, such as inflammation, instability or fracture. In a preferred embodiment, the liquid medium comprises a low viscosity cyanoacrylate-based adhesive.

20 Claims, 2 Drawing Sheets

METHOD OF SPINAL FIXATION USING ADHESIVE MEDIA

BACKGROUND OF THE INVENTION

1. Field of the Invention

The present invention relates to a method of spinal fixation involving application of a liquid medium which cures, hardens, polymerizes or otherwise serves to bind adjacent vertebrae together. The fixation which results from this binding may be temporary or essentially permanent in duration.

2. Description of the Related Art

The spinal vertebrae are separated by cartilage disks, filled with a gelatinous substance, that provide cushioning to the spinal column. These disks may herniate or rupture from trauma or strain, especially if degenerative changes have occurred in the disk.

A herniated intervertebral disk, also known as a slipped or ruptured disk, is a condition in which part or all of the soft, gelatinous nucleus pulposus in the central portion of an intervertebral disk is forced through a weakened part of the annulus fibrosis, resulting in back pain and nerve root irritation.

Most herniation takes place in the lumbar area of the spine. Lumbar disk herniation occurs 15 times more often than cervical disk herniation, and it is one of the most common causes of lower back pain. The cervical disks are affected 8% of the time and the thoracic disks only 1 to 2% of the time. When lumbar disk herniation occurs, nerve roots, the large nerves that branch out from the spinal cord, may become compressed resulting in neurological symptoms such as pain or weakness in the back and lower extremities.

Although minor cases of disk herniation may be treated with bed rest and medications to relieve pain and reduce inflammation, surgery may be indicated for people who fail to respond to bed rest and medications.

One common type of surgery performed to alleviate back pain is discectomy. Discectomy involves the surgical removal of the diseased disc, thereby relieving the pressure. In spite of the fact that the procedure has been done for many years, few studies have been conducted to determine its real effectiveness. Scar tissue may develop after discectomy, which, in some cases, can cause continued pain.

Another common procedure is spinal fusion. Spinal fusion involves making a percutaneous incision or puncture over the affected area of the spine and joining the vertebrae together using bone grafts and/or rods made of metal or other materials of substantial strength.

Another procedure performed is laminectomy. Laminectomy is performed to remove the protruding disk. This procedure involves removing the bone that curves around and covers the spinal cord (lamina) and the tissue that is causing pressure on the nerve or spinal cord.

Complications of spinal surgery can include nerve and muscle damage, infection, scarring, and the need for re-operation. Patients often remain hospitalized for several days after surgery, and in bed for anywhere from a few days to a few weeks following surgery. A back brace or cast may be necessary for weeks following the surgery to immobilize the spine until the fusion has occurred.

SUMMARY OF THE INVENTION

In accordance with one preferred embodiment, there is provided a method of temporary spinal fixation. The method comprises identifying a first and a second adjacent surfaces in a spine, the first and second surfaces in sliding contact with each other at a joint and introducing a medium between the first and second surfaces which undergoes a physical or chemical change to immobilize the joint.

In accordance with another preferred embodiment, there is provided a method of immobilizing a portion of the spine. The method comprises identifying a joint between a first vertebra and a second vertebra which is to be immobilized, and administering an adhesive medium to bond at least a first superior articular process on the first vertebra to a corresponding first inferior articular process on the second vertebra, wherein the medium comprises cyanoacrylate.

In accordance with another preferred embodiment, there is provided a method of treating inflammation in the spine. The method comprises identifying a joint between a first vertebra and a second vertebra which is in the vicinity of an inflammation, and administering an adhesive medium to bond at least a first superior articular process on the first vertebra to a corresponding first inferior articular process on the second vertebra to temporarily immobilize the joint for a sufficient time to treat the inflammation, wherein the administering step is accomplished without a surgical cut down.

In accordance with still another preferred embodiment, there is provided a method of immobilizing a portion of the spine. The method comprises identifying a joint between a first vertebra and a second vertebra which is to be immobilized, and administering a thin film of a medium comprising an adhesive within the joint to bond at least a first superior articular process on the first vertebra to a corresponding first inferior articular process on the second vertebra.

DETAILED DESCRIPTION OF THE PREFERRED EMBODIMENT

Figure 1:
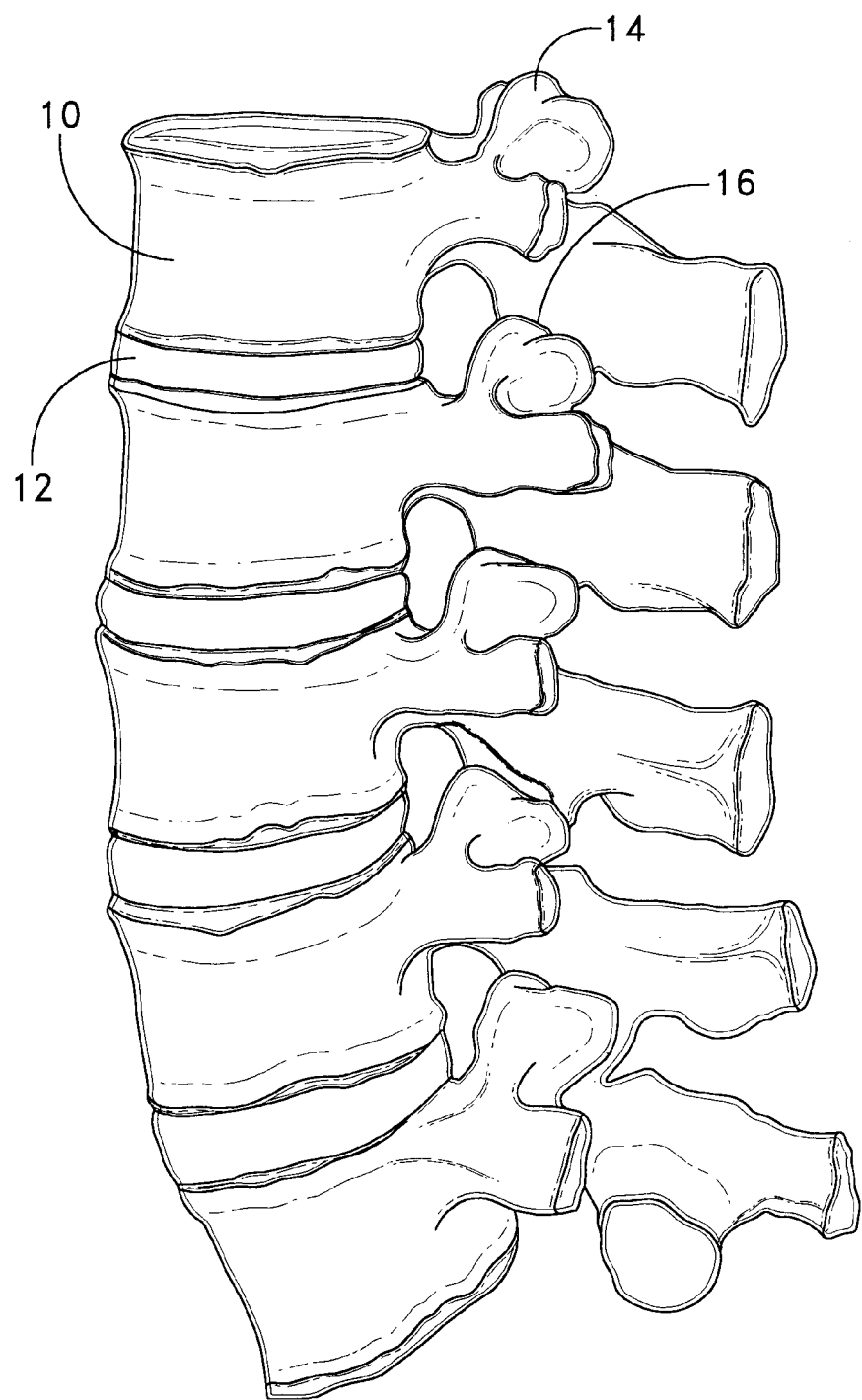
FIG. 1 is a left lateral view of the lumbar region of the human spine.

The present invention relates to a method of spinal fixation involving application of a liquid medium which cures, hardens, polymerizes or otherwise serves to bind adjacent vertebrae together. The fixation which results from this binding may be temporary or essentially permanent in duration, and may be used to treat inflammation, disk herniation, and/or fracture or instability in the spine.

The terms "medium" and "media" as used herein, refer to the liquid material used according to preferred embodiments herein to join one or more adjacent vertebrae. Preferred media comprise an adhesive, which is used in a broad sense to include single component or multiple component materials, curable compositions, polymerizable compositions, cements, as well as other types of materials or compounds, presently known or later-developed, which may be used to join, bond or adhere surfaces or materials together. Suitable adhesives include both biological and non-biological adhesives. The class of materials referred to herein as adhesives includes curable compositions, including, but not limited to those which cure by mixing two or more component parts, those which cure by cross-linking, and those which cure in the presence of some activator, accelerant or catalyst, including, but not limited to water, heat, chemicals, or radiation. Adhesives also include polymerizable compositions, which preferably comprise one or more monomers or oligomers which polymerize or further polymerize following application to the desired site. A medium may consist solely of or essentially of one or more adhesives, or it may further comprise one or more additional materials. Additional materials include those which modify properties of the adhesive, as well as those which impart other desirable properties or characteristics to the medium.

Examples of preferred adhesives include cyanoacrylates, epoxies, fibrin-based adhesives, as well as other presently known or later-developed materials suitable for use in the methods disclosed herein. Polymerizable adhesives that have been cross-linked or co-polymerized with other compounds that may alter elasticity, modify viscosity, aid biodegradation or change some other property of the resulting material may be used in media. For example, polyacrylic acid may be cross-linked to a cyanoacrylate to form compounds which may allow for greater bioabsorbability.

Cyanoacrylates are among the preferred adhesives used in media as disclosed herein. Among the reasons why cyanoacrylates are preferred are that they can harden almost instantaneously on contact with surfaces having moisture thereon, including most tissues and surfaces in the body of an animal, such as a human. Preferred cyanoacrylates include, but are not limited to, methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropyl cyanoacrylate, 2-methoxypropyl cyanoacrylate, 3-chloropropyl cyanoacrylate, benzyl cyanoacrylate, phenyl cyanoacrylate, alkenyl cyanoacrylate, butyl-2-cyanoacrylate, alkoxyalkyl 2-cyanoacrylates, fluorinated 2-cyanoacrylates, and carbalkoxyalkyl cyanoacrylates, depending upon acceptable toxicity and other properties for a given application. More preferably the adhesive compound comprises ethyl cyanoacrylate or butyl-2-cyanoacrylate. These latter two compounds, are available commercially from Loctite Corporation (Hartford, Conn.) or Pacer Technology (Rancho Cucamonga, Calif.). Other members of the cyanoacrylate family may be commercially available or may be synthesized according to published procedures or analogous methods as is within the abilities of one skilled in the art. Also suitable are commercially available cyanoacrylate based tissue adhesives such as Dermabond® (Johnson & Johnson, New Brunswick, N.J.).

Preferred fibrin-based adhesives include those which include components having human, animal or recombinant origin. Such adhesives include, but are not limited to, adhesives comprising thrombin and fibrinogen delivered separately or mixed at the site to be bonded, adhesives comprising fibrinogen and Factor XIII, adhesives produced near the time of use from autologous components, and adhesives as described in U.S. Pat. Nos. 6,019,993, 6,063,297, 5,716,645, 5,962,405, 5,605,887, 5,883,078, and 5,464,471, the disclosures of which are incorporated herein by reference in their entireties. Also suitable are commercially available fibrin based adhesives, including Tissucol® (Immuno A. G., Vienna, AT) and Tisseel® (Baxter Healthcare Corp., Deerfield, Ill.).

Media employed in preferred embodiments may comprise components and materials in addition to adhesive. Such other components include, but are not limited to, inhibitors, activators, catalysts, colorants, dyes, including colored dyes, radioscopic dyes and fluoroscopic dyes, radiopaque components, drugs, viscosity modifiers, and wetting agents. In one preferred embodiment, a medium comprises a cyanoacrylate and a low viscosity inhibitor. One preferred low viscosity inhibitor is sulfur dioxide. Such embodiments preferably have a very low, water-like viscosity such that capillary action or the natural wetting action can cause the medium to be pulled in to a thin opening, including the space between the articular processes which are coated with smooth, slippery cartilage or other such slidable areas to be fused.

In discussing the viscosity of the media in the context of the preferred embodiments, the viscosity referred to generally is the viscosity of the medium at the time it is being applied. Following application, the medium will increase in viscosity until it "sets up" to a final solid or relatively solid state due to the action of one or more physical or chemical mechanisms in the medium, including, but not limited to curing, cross-linking, polymerizing, hardening, and evaporation of solvent. Once the medium has set up, it preferably takes a solid form, which may be somewhat flexible or may be relatively stiff. In one embodiment, the pre-application or application time viscosity of a medium is preferably about 10–50,000 centipoise (cp), more preferably about 10–5,000 cp or 10–100 cp, including about 20 cp, about 30 cp, about 50 cp, and about 75 cp. Media having viscosities outside of these stated ranges and values may also be suitable, depending upon one or more of several factors, including, but not limited to the location and method of application. In a preferred embodiment, the medium has a viscosity sufficiently low to permit it to be pulled into a small gap between surfaces under capillary action.

It is preferred that media used in the methods described herein exhibit a good ability to coat or wet the surfaces of the spine to which they are applied so as to aid application and creation of a firm and even bond.

Another characteristic of a medium is the time required for the medium to set up to the point where a reasonable degree of fixation or immobilization of the target region of the spine is achieved. A reasonable degree of fixation is generally thought to be achieved when at least moderate movement of the back area of the patient does not disrupt the bond. Once it has set up, a medium may still undergo further polymerization, reaction, curing, hardening or other chemical or physical phenomenon to achieve a final state or bond. It is preferred that the set up time is fairly short, so as to shorten the overall time of the procedure. A short set up time also allows the physician (or other such practitioner) to confirm that the fusion or immobilization has occurred properly. It is also preferred, however, that the set up time not be too short as to interfere with the physician's need to adjust or position the vertebrae and/or other surfaces being joined during the procedure. In one embodiment, the set up time is preferably less than about 20 minutes, less than about 10 minutes, or less than about 5 minutes, including about 10 seconds to about 10 minutes, and about 30 seconds to about 2 minutes. Media having set up times outside of these stated ranges and values may also be suitable, depending upon one or more of several factors, including, but not limited to the method of application and the time needed to properly position the spine.

The set up time can be altered by choice of adhesive in the medium. Additionally, for a given adhesive, the set up time can be increased or decreased by the use of (or by varying the amounts of) catalysts, activators, inhibitors, monomers, and other such components in the medium.

Depending upon the length of time it is desired for the vertebrae to be fixed together, the degree of biodegradability or bioabsorbability in the medium employed may be varied. For example, if temporary fixation is desired, such as for a period of weeks or months, a higher degree of biodegradability or bioabsorbability in the medium is desired. Temporary fixation can be for a period of about 1 to 12 months, or 1 to 5 weeks, although longer and shorter periods of time are also contemplated. If, however, more permanent fixation is desired, such as for a period of several years, it is preferable to use a medium that is only slowly degradable or substantially nonbiodegradable. Permanent or semi-permanent fixation can be for a period of about 1 to 10 years, although longer or shorter periods of time are also contemplated. Modes of degradation or dissipation of the medium in the body over time following fixation include, but are not limited to, those which occur due to the presence of heat, water or aqueous fluids, enzymes or other active compounds, physical stress and/or shear forces. Degradation or dissipation may also result from a combination of modes.

There is a wide variation in the rates and facility of in vivo biodegradation of polymers made from monomers which may be used in media according to preferred embodiments. Generally, cyanoacrylates and other adhesives that have substituents that are small and/or contain one or more oxygen-containing functional groups (e.g. ether, ester, carbonyl) appear to have increased biodegradability rates. Conversely, cyanoacrylates and other adhesives having long chain alkyl groups lacking in oxygen-containing or polar functional groups as substituents may tend to form polymers that biodegrade more slowly. There are also indications that the biodegradation rate of polymer-based adhesives is affected by the polymer molecular weight and crystallinity of the polymer, with higher molecular weight and higher crystallinity generally indicating a more stable, less degradable material.

To effectively immobilize or reduce the mobility of the targeted region of the spine, a medium is applied to abutting or adjacent surfaces in at least two adjacent vertebrae. Such surfaces preferably move with respect to each other by sliding, rocking, or other such movement which occurs in a normally functioning spine. In accordance with one embodiment, at least one medium is applied to one or more adjacent surfaces, followed by bringing the surfaces together. In a preferred embodiment, at least one medium is applied to form a film or layer or to fill a space between the surfaces. Following application, the film or layer preferably covers the entirety of the surfaces so as to have a larger, but preferably still thin, bonding surface and achieve a stronger bond. Similarly, if the application of medium entails filling a space, it is preferred that substantially the entire space be filled so as to maximize bonding force. Following the application of media and any time needed for set up, curing, or other physical and/or chemical changes, the surfaces and/or the vertebrae to which they are attached should be substantially prevented from moving relative to each other.

In a preferred embodiment, the introduction or application of medium to a site is effected using a tubular introducer, including, but not limited to a cannula, needle or other hollow structure. The term "tubular" is intended to convey that preferred introducers are elongate, hollow structures which allow for the passage of media through the hollow space, rather than to convey any particular shape or profile. Accordingly, an introducer may have any suitable cross-sectional shape including circular, ovoid, ellipsoid, polygonal, etc. In one embodiment, a first end of the introducer is attached to a reservoir or container which provides for storage of medium before and/or during application. A second end of the introducer is preferably shaped into or fitted with a relatively fine tip to aid in precise application of media. In an especially preferred embodiment, the second end of the introducer is a needle-type point which also can readily puncture the skin to aid in percutaneous application of the medium.

Media is expressed through the introducer using any suitable means, including, for example, pressure, gravity, and capillary action. One end of the introducer is placed at the desired location and the medium is then applied or expressed in the desired quantity. The medium may be expressed directly into a target joint or capsule or onto one or more surfaces. For example, the tip of the introducer may be placed near the center of a joint and the medium expressed. Alternatively, the tip of the introducer may be placed within a capsule or other space and the medium expressed to substantially fill, or at least partially fill, the space. The medium may also be expressed near the edge of a joint, space or surface and then be forced by the flow of material into the joint, space or surface. If a low viscosity medium is used, the medium may be expressed near the edge of a joint, space, or surface or it may be placed in contact with same, allowing the medium to be drawn into the joint, space or surface by means of capillary action.

Figure 2:
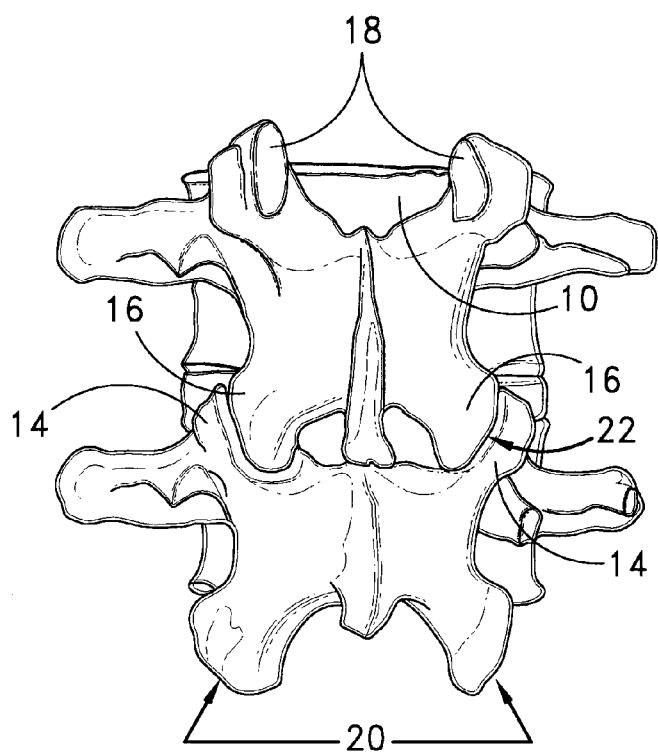
FIG. 2 is a posterior view of the third and fourth lumbar vertebra of the human spine.

In a preferred embodiment, two or more vertebrae are fused together. Referring to FIG. 1 the lumbar region of the spine, containing five vertebrae (L1–L5), is illustrated in a left lateral view. A posterior view of the third and fourth lumbar vertebrae (L3–L4) is illustrated in FIG. 2. Both FIGS. 1 and 2 are dissections which show primarily only the bony portions and the intervertebral disks. Although the lumbar spine is shown, the techniques and methods disclosed herein may be used in or adapted to other locations in the spine. Furthermore, these techniques may be used and adapted for use in repair of bones and/or cartilage in other parts of the body.

Each vertebra comprises a generally cylindrical vertebral body 10 which is separated from its adjacent vertebrae by intervertebral disks 12. Each vertebra further comprises several processes, among them the superior and inferior articular processes. The two superior articular processes 14 of each vertebra project upward and the two inferior articular processes 16 of each vertebra project downward. The superior articular processes 14 are wider apart than the inferior articular processes 16, since, when placed together in the spinal column, the inferior articular processes 16 of one vertebra are embraced by the superior processes 14 of the subjacent vertebra. Each superior process 14 terminates in a facet 18 which is concave and looks backward and medialward. Each inferior process 16 terminates in a facet 20 which is convex and directed forward and lateralward. The facets 18 of the superior processes 14 of one vertebra thus mate with the facets 20 of the inferior processes 16 of the vertebra directly above to form a zygapophyseal joint 22 where each pair of corresponding articular processes meet. Although not shown in the figures, there is a ligament which extends from the inferior process of one vertebra to the superior process of the vertebra immediately below, encapsulating the zygapophyseal joint 22 in what is known as the capsule of the zygapophyseal joint.

In accordance with one preferred embodiment, a medium is applied to one or both zygapophyseal joints between a pair of vertebrae. The application may occur within the joint, or the medium may be applied primarily to a facet of a superior process of one vertebra and/or to the corresponding facet of the inferior process of the superjacent vertebra. It is preferred that enough media be applied to at least form a film or layer over the entire surface area of a joint or facet, although smaller or larger amounts of medium may be used.

In an alternate embodiment, the medium is placed into the capsule of the zygapophyseal joint to substantially fill, or at least partially fill the capsule with medium. In this manner, the capsule may be used both as a means of containing the medium and also as a way of extending the surface area over which the fusing bond acts.

As noted above, the fixation or bonding involving the articular processes between two vertebrae may be either unilateral (one pair of articular processes) or bilateral (both pairs of articular processes). Furthermore, this process can be repeated to provide for the fixation of more than one pair of vertebrae in a single spine. The multiple fixation points may be in adjacent groups of vertebrae, or they may be non-contiguous. In preferred embodiments, the vertebrae which are fixed together are in the lumbar region of the spine, and may also include fixation to the first vertebra of the adjacent sacral region. In one embodiment, all five vertebrae which constitute the lumbar region are fixed together.

The fixation methods described above which involve the articular processes may be performed alone, or it may be combined with other techniques of fusing or fixing the spine. For example, a medium may be used to fix the articulate processes in combination with use of rods or wires to fix the vertebral bodies. Alternatively, use of a medium to fix the articulate processes may be combined with methods which involve stimulating the growth of a bony mass or fusion body to fix the spine. The fixation provided by the medium can provide extra support and stability to the spine so as to increase the chances of having successful fusion provided by the growth of bone.

Fixation of the spine need not be confined to the articular processes. Other adjacent portions of adjoining vertebrae may be fixed using a medium. For example, a medium could be applied to fix adjacent vertebral bodies. One such method could involve applying a medium to the adjacent vertebral bodies and/or the intervertebral disk (or artificial disk replacement) which separates them. Alternatively, a medium could be applied to adjacent vertebral bodies to stabilize them following discectomy.

Although many statements herein refer to preferred embodiments in which one medium is applied, it is presently contemplated that more than one medium may be applied, either in concert or in series.

The temporary or more permanent fixation that results from application of preferred methods disclosed herein may be used to treat conditions including, but not limited to, inflammation, disk herniation, instability, and fracture. The immobilization which results from fixation can provide an environment in which spinal inflammation is reduced and in which a disk may heal itself, either entirely or enough to reduce or eliminate the symptoms of disk herniation. The fixation can provide stabilization of a region in the spine to allow for strengthening of the muscles and other tissues in the spine through physical therapy, growth of a stable fusion body, and the like to provide longer term repair and relief. Even if a procedure must be repeated periodically, preferred procedures, especially percutaneous procedures, are less invasive and less traumatic than conventional surgical procedures. Similarly, procedures described herein may also be used as a "bridge" to a more extensive surgical procedure, providing for an alleviation of symptoms, lessening of pain, provision of stability to the spine and/or other such aid to the patient on a temporary basis until such surgical procedure can be performed.

In some embodiments, application of a medium to one or more locations is done in a surgical procedure. The surgical procedure may involve only the fixation by means of medium, or it may be done in combination with other procedures, including, but not limited to discectomy, fusion, and laminectomy. Such other surgical techniques involving the spine may be enhanced or improved by incorporation of techniques involving fixation using a medium as described herein.

Alternatively, fixation using a medium may be performed percutaneously, without surgical cut-down, whether performed alone or in combination with some other technique or procedure, including, but not limited to, discectomy and application of a medicament. In one preferred embodiment, fixation is performed percutaneously with the spine and introducer being monitored and guided using fluoroscopy. Use of fluoroscopy to visualize the spine and deliver drugs or perform a spinal puncture is known and widely used. These same techniques can be adapted to visualize and guide the introducer to the desired location, be it a joint, capsule, surface or otherwise, to apply a medium. In a procedure using fluoroscopy, it is preferred that the medium contains a fluoroscopic dye or other agent to enable the medium to be visualized during the procedure, which allows the physician to monitor both the amount of medium delivered and the location of delivery. Techniques other than fluoroscopy which allow visualization of the spine and introducer including, but not limited to, ultrasound, may also be used in connection with preferred percutaneous procedures.

Both surgical and percutaneous methods may further include a step of aligning the spine prior to introducing the medium to help ensure that the vertebrae will have proper positioning and alignment when fixed. Preferred methods may include the additional step of providing an anesthetic, such as an epidural anesthetic, prior to initiating the introduction of medium or other aspects of a procedure.

One preferred embodiment involves a method of temporary spinal fixation. The method comprises identifying first and second adjacent surfaces in the spine that are in contact with each other at a joint, and introducing a medium between the first and second surfaces (which may include one or both such surfaces) or into the joint. The medium preferably then undergoes a physical or chemical change to fix or immobilize the joint. For such temporary fixation, it is preferred that media used are susceptible to biodegradation or bioabsorption.

In accordance with another preferred embodiment, there is a method of immobilizing a portion of the spine. The method comprises identifying a joint between two vertebrae which is to be immobilized, and administering an medium to bond at least one surface on a first vertebra and an adjacent surface on the second vertebra, preferably a first superior articular process on one vertebra and the corresponding inferior articular process on the second vertebra.

In another preferred embodiment, there is provided a method of treating inflammation in the spine. The method comprises identifying a joint between a first vertebra and a second vertebra that is in the vicinity of an inflammation, and administering a medium to bond at least one surface, preferably a first superior articular process, on the first vertebra to an adjacent second surface, preferably the corresponding first inferior articular process, on the second vertebra to temporarily immobilize the joint for a sufficient time to treat the inflammation, wherein the administering step is preferably accomplished without a surgical cut down.

The procedures described herein may be coupled with epidural administration of one or more anti-inflammatory agents, including, but not limited to, cortisone and other steroidal compounds. In preferred embodiments, the administration of the medium and/or the anti-inflammatory agent is performed using fluoroscopy to aid in placement at the desired site.

Figure 3:
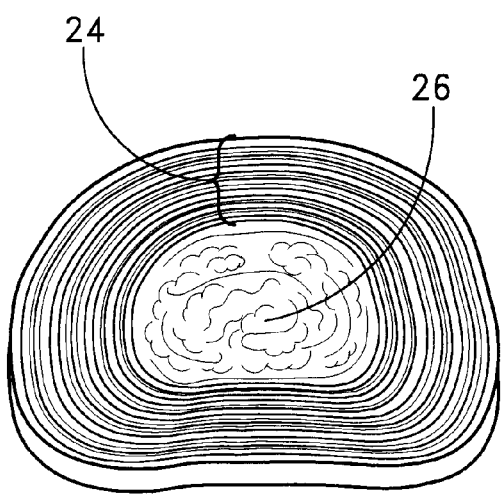
FIG. 3 is a superior view of an intervertebral disk.

Media may also be used to repair or augment the intervertebral disks. As shown in FIG. 3, a disk 12 comprises two main regions: the annulus fibrosis 24 and the nucleus pulposus 26. The nucleus pulposus 26 comprises a relatively soft gelatinous material that acts as a "shock absorber" in the spine. It is surrounded and protected by the annulus fibrosis 24, a ring of relatively tough tissue. Herniation occurs when some, or even substantially all, of the nucleus pulposus is forced through a split, rupture, or weakened area of the annulus fibrosis.

Although, as noted above, it is believed that small ruptures in a disk can heal if the spine is rested or immobilized in the region of the injured disk, larger ruptures in which there has been an expulsion of larger amounts of pulpous material are not currently believed to be capable of self-repair. If the enucleated material is of a sufficient quantity to result in a change in the shape or size of the disk, instability of the spine may result. In such circumstances, it may be desirable to add medium to the disk to augment any remaining nucleus pulposus. Preferably the medium used in such augmentation has elastic or resilient properties to mimic the natural contents of the nucleus pulposus. Adhesive properties of the medium can help the medium stay in place inside the annulus fibrosis. Preferably the medium is expressed into the interior of the disk using a tubular introducer. This procedure may be performed percutaneously or surgically, and may be done in combination with removal of enucleated pulpous material and/or with any of the aforementioned fixation techniques.

In addition to augmenting the nucleus, application of a medium may be used repair the tear, hole, or other such disruption in the annulus fibrosis through which enucleation occurred. Such medium may be of a similar or different composition as the medium used to augment the nucleus pulposus. Alternatively, in those cases where sufficient natural pulpous material remains in the disk, a medium may be used to repair tears, holes, and other disruptions in the annulus fibrosis with minimal or no augmentation of the nucleus. In such situations, the adhesive properties of the medium allow for repair or sealing of the damaged annulus when it is applied to one or more surfaces thereof.

The various methods and techniques described above provide a number of ways to provide fixation or immobilization of at least a portion of the spine. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. A method of immobilizing a portion of the spine, comprising the steps of identifying a joint between a first vertebra and a second vertebra which is to be immobilized, and administering an adhesive medium to bond at least a first superior articular process on the first vertebra to a corresponding first inferior articular process on the second vertebra, wherein the adhesive comprises cyanoacrylate and a radio opaque component.

2. A method of immobilizing a portion of the spine as in claim 1 further comprising the step of administering an adhesive medium to bond a second superior articular process on the first vertebra to a corresponding second inferior articular process on the second vertebra.

3. A method of immobilizing a portion of the spine as in claim 1, wherein the adhesive further comprises a polymerization inhibitor.

4. A method of immobilizing a portion of the spine as in claim 3, wherein the adhesive has a viscosity of no more than about 100 centipoise.

5. A method of immobilizing a portion of the spine as in claim 1, wherein the administration step is accomplished percutaneously.

6. A method of treating inflammation in the spine, comprising the steps of identifying a joint between a first vertebra and a second vertebra which is in the vicinity of an inflammation, and administering an adhesive medium comprising a radio opaque component to bond at least a first superior articular process on the first vertebra to a corresponding first inferior articular process on the second vertebra to temporarily immobilize the joint for a sufficient time to treat the inflammation, wherein the administering step is accomplished without a surgical cut down.

7. A method of treating inflammation in the spine as in claim 6, further comprising the step of administering an adhesive medium to bond a second superior articular process on the first vertebra to a corresponding second inferior articular process on the second vertebra.

8. A method of treating inflammation in the spine as in claim 6, further comprising the step of permitting the adhesive to dissipate following a treatment period of time.

9. A method of treating inflammation in the spine as in claim 8, wherein the treatment period is within the range of from about one week to about six months.

10. A method of treating inflammation in the spine as in claim 6, wherein the administering step is accomplished percutaneously.

11. A method of treating inflammation in the spine as in claim 6 wherein the adhesive further comprises cyanoacrylate.

12. A method of treating inflammation in the spine as in claim 6, wherein the joint is in the lumbar region of the spine.

13. A method of treating inflammation in the spine as in claim 6, wherein the joint is in the sacral region of the spine.

14. A method of treating inflammation in the spine as in claim 6, wherein the joint is in the L4-L5-S1 region of the spine.

15. A method of treating inflammation in the spine as in claim 6, wherein the administering step comprises expressing the adhesive near an edge of the joint, and permitting the adhesive to enter the joint by capillary action.

16. A method of treating inflammation in the spine as in claim 6, wherein the administering step comprises positioning a distal end of an injection needle within the joint and expressing adhesive under pressure within the joint.

17. A method of treating inflammation in the spine as in claim 6, wherein the administering step is accomplished under fluoroscopy.

18. A method of treating inflammation in the spine as in claim 6, further comprising the step of augmenting a spinal nucleus at the level of the joint.

19. A method of treating inflammation in the spine as in claim 6, further comprising the step of aligning the spine prior to the administering step.

20. A method of immobilizing a portion of the spine, comprising the steps of identifying a joint between a first vertebra and a second vertebra which is to be immobilized, and administering a thin film of adhesive medium within the joint to bond at least a first superior articular process on the first vertebra to a corresponding first inferior articular process on the second vertebra, wherein the adhesive medium comprises a radio opaque component.

* * * * *